US006913744B2

(12) United States Patent
Gokcen

(10) Patent No.: US 6,913,744 B2
(45) Date of Patent: *Jul. 5, 2005

(54) METHOD AND COMPOSITION FOR TREATING PROSTATE CANCER

(75) Inventor: Muharrem Gokcen, Minneapolis, MN (US)

(73) Assignee: Immunolytics Inc., Minneapolis, MN (US)

( * ) Notice: Subject to any disclaimer, the term of this patent is extended or adjusted under 35 U.S.C. 154(b) by 214 days.

This patent is subject to a terminal disclaimer.

(21) Appl. No.: 10/055,063

(22) Filed: Jan. 22, 2002

(65) Prior Publication Data

US 2002/0061300 A1 May 23, 2002

Related U.S. Application Data

(63) Continuation of application No. 09/428,375, filed on Oct. 28, 1999, now Pat. No. 6,428,785.

(51) Int. Cl.[7] .......................... A61K 38/43; A61K 38/54; A61K 38/46

(52) U.S. Cl. .................. 424/94.1; 424/94.2; 424/94.62; 424/94.67

(58) Field of Search ............................. 424/94.1–94.67

(56) References Cited

U.S. PATENT DOCUMENTS

| 4,524,065 | A | 6/1985 | Pinnell |
| 4,645,668 | A | 2/1987 | Pinnell |
| 4,678,668 | A | 7/1987 | Darras |
| 4,978,332 | A | 12/1990 | Luck et al. |
| 5,051,257 | A | 9/1991 | Pietronigro |
| 5,116,615 | A | 5/1992 | Gokcen et al. |
| 5,162,115 | A | 11/1992 | Pietronigro |
| 5,422,261 | A | 6/1995 | Lee et al. |
| 5,424,208 | A | 6/1995 | Lee et al. |
| 5,567,417 | A | 10/1996 | Sasisekharan et al. |
| 5,658,730 | A | 8/1997 | McGill et al. |
| 5,753,485 | A | 5/1998 | Dwulet et al. |
| 5,780,435 | A | 7/1998 | Garnick et al. |
| 5,783,182 | A | 7/1998 | Thompson |
| 5,830,741 | A | 11/1998 | Dwulet et al. |
| 5,843,902 | A | 12/1998 | Garnick et al. |
| 5,854,206 | A | 12/1998 | Twardzik et al. |
| 5,952,215 | A | 9/1999 | Dwulet et al. |
| 5,989,888 | A | 11/1999 | Dwulet et al. |

FOREIGN PATENT DOCUMENTS

| WO | WO 90/08555 | 8/1990 |
| WO | WO 97/10842 | 3/1997 |

OTHER PUBLICATIONS

Murphy et al., Clinical Oncology, 2nd edition, American Cancer Society, 1995, pp. 315–318.*

Baert, L, et al., "Treatment of Chronic Bacterial Prostatitis by Local Injection of Antibiotics into Prostate", *Urology*, vol. XXL, No. 4, pp. 371–375 (Apr. 1983).

Cawston, T. et al., "Mammalian Collagenases", *Methods in Enzymology*, vol. 80, pp. 711–722 (1981).

Chang, N., "Transforming Growth Factor–Beta Protection of Cancer Cells Against Tumor Necrosis Factor Cytotoxicity is Counteracted by Hyaluronidase", *J. Mol. Med.*, vol. 2, No. 6, pp. 653–659 (Dec. 1998) (Abstract Only).

Darson, M. et al., "Transurethral Enzyme Injection—Future Management of Benign Prostatic Hyperplasia", *Mayo Clin Proc*, vol. 73, pp. 908–911 (1998).

Giovannucci, E. et al., "Calcium and Fructose Intake in Relation to Risk of Prostate Cancer", *Cancer Research*, vol. 58, pp. 442–447 (Feb. 1, 1998).

Harmon, W. et al., "Transurethral Enzymatic Ablation of the Prostate: Canine Model", *Urology*, vol. 48, No. 2, pp. 229–233 (Aug. 1996).

Liu , A. et al., "Cell–cell Interaction in Prostate Gene Regulation and Cytodifferentiation", *Proc. Natl. Acad. Sci. USA*, vol. 94, No. 20, pp. 10705–10710 (Sep. 30, 1997).

Lokeshwar, V. et al., "Association of Elevated Levels of Hyaluronidase, a Matrix–degrading Enzyme, with Prostate Cancer Progression", *Cancer Res.*, vol. 56, No. 3, pp. 651–657 (Feb. 1, 1996) (Abstract Only).

Longo, F. et al., "Collagenase as an Adjunct to Cryoprostatectomy", *Collagenase*, Editor: I. Mandl,, Gordon & Breach, New York, New York, pp. 113–120 (1972).

Marieb, E., *Human Anatomy and Physiology*, Second Edition, The Benjamin/Cummings Publishing Company, Inc., p. 936, (1992).

Nagle, R. et al., "Adhesion Molecules, Extracellular Matrix, and Proteases in Prostate Carcinoma", *Journal of Cellular Biochemistry*, Supplement 19, pp. 232–237 (1994).

(Continued)

*Primary Examiner*—Gary B. Nickol
(74) *Attorney, Agent, or Firm*—Merchant & Gould P.C.

(57) ABSTRACT

A method of treating prostate cancer in a living mammal includes local administration of a composition that includes a therapeutically effective concentration of collagenase. In one embodiment, a method of treating prostate cancer in a living mammal includes local administration of a composition that includes a therapeutically effective concentration of collagenase and at least one of a glycosidase, a protease, a nuclease, a lipase, an esterase, a plasminogen activator, a streptokinase, and combinations thereof. Preferably a glycosidase, such as, for example, hyaluronidase, is administered. Compositions used in methods for treating prostate cancer can also include or be administered with calcium ions, a nonionic surfactant, such as, for example, Triton® X-100, and an antibiotic, such as, for example, gentamicin. Another method of treating prostate cancer in a living mammal includes activating PSA in vivo by, for example, locally administering calcium ions.

22 Claims, No Drawings

OTHER PUBLICATIONS

Partsch, G. et al., "High Free and Latent Collagenase Activity in Psoriatic Arthritis Synovial Fluids", *British Journal of Rheumatology*, vol. 33, No. 8, pp. 702–706 (Aug. 1994).

Presnell, S. et al., "Isolation and Characterization of Propagable Cell Lines (HUNC) from the Androgen–sensitive Dunning R3327H Rat Prostatic Adenocarcinoma", *Carcinogenesis*, vol. 19, No. 4, pp. 585–590 (Apr. 1998).

Saltus, R., "The Answer for Cancer?", *Popular Science*, pp. 52–55 (Jan. 1999).

Sehgal, I. et al., "Transforming Growth Factor Beta1 Stimulates Contrasting Responses in Metastatic Versus Primary Mouse Prostate Cancer–derived Cell Lines in Vitro", *Cancer Res.*, vol. 56, No. 14, pp. 3359–3365 (Jul. 15, 1996) (Abstract Only).

VanDeGraff, K. et al., *Concepts of Human Anatomy and Physiology*, Wm. C. Brown Publishers, p. 938 (1986).

"NCI Publication—What You Need To Know About (tm) Prostate Cancer", http://cancernet.nci.nih.gov/wyntk_pubs/prostate.htm, 25 pages (Dec. 12, 2000).

"Prostate Cancer", http://www.cancerpage.com/articles/default.asp?id=3&subarea=Your_Illness, 4 pages (Nov. 9, 2000).

"Prostate Enlargement: Benign Prostatic Hyperplasia", http://www.niddk.nih.gov/health/urolog/pubs/prostate/index.htm, 15 pages (Jan. 2000).

* cited by examiner

METHOD AND COMPOSITION FOR TREATING PROSTATE CANCER

This application is a continuation of application Ser. No. 09/428,375, U.S. Pat. No. 6,428,785, filed Oct. 28, 1999, which application(s) are incorporated herein by reference.

FIELD OF THE INVENTION

The present invention is directed to a method for treating prostate cancer by administering collagenase alone or in combination with a glycosidase, a protease, a nuclease, a lipase, an esterase, a streptokinase, or a combination thereof. A typical embodiment includes administering a composition including a mixture of collagenase, hyaluronidase, a non-ionic surfactant, an antibiotic, and calcium ions.

BACKGROUND OF THE INVENTION

Approximately ten million American men are believed to have prostate cancer today. Although fewer than 3% of men with the disease die from it, prostate cancer still is the second most common cause of cancer death among men. The cancer usually is localized in the prostate, but in some cases, the cancer is not diagnosed until it has metastasized to the bone, kidneys, or the brain.

Yearly screening for the disease increases the likelihood of early detection, especially prior to the disease metastasizing. Such screening usually involves a digital rectal exam and a prostate-specific-antigen (PSA) blood test. Other screening methods include ultrasound imaging, radionucleid scan, and biopsy.

The PSA blood test has revolutionized the early diagnosis of prostate cancer and the effectiveness of treatment. PSA is a proteolytic enzyme in the family of serine proteases and one of the most abundant proteins in the prostate secretions. PSA is synthesized in the ductal epithelium and prostatic acini and is located within the cell in cytoplasmic granules and vesicles, rough endoplasmic reticulum, vacuoles, secretory granules, and lyosomal dense bodies. PSA is secreted into the lumina of the prostatic ducts where it becomes a component of seminal plasma. To reach blood serum, PSA diffuses from luminal cells through the epithelial basement membrane and prostatic stroma and either passes through the capillary basement membrane and epithelial cells or into the lymphatics. Once in the bloodstream, the majority of PSA forms complexes with α-1-antichymotrypsin (PSA-ACT) and α-2-macroglobulin, while small quantities remain free (free PSA). Free PSA levels are usually elevated in instances of prostate cancer.

Once prostate cancer is diagnosed, a suitable method of treatment must be determined and then administered. Current methods of treatment include radical prostatectomy, radiation, and hormonal suppression. To determine the appropriate method of treatment, factors such as the age of the patient and severity of the disease are often considered. The disease generally is more aggressive for younger patients. Any tumor greater than 0.5 cc is typically considered clinically significant. The preferred treatment for localized prostate cancer is radical prostatectomy. This treatment may result in death, incontinence, impotence, rectal injury, or pulmonary emboli.

Thus, it is desirable to provide improved methods of treatment for prostate cancer that reduce the likelihood of one or more of these unpleasant side effects. In particular, it is desirable to provide improved methods of treatment that reduce the likelihood of the treatment rendering the patient impotent.

SUMMARY OF THE INVENTION

The current invention is directed to a method of treating prostate cancer in a living mammal. In one aspect, the treatment is directed to activating PSA in vivo. PSA in or near the prostate can be activated by one of several methods, such as by local administration of calcium ion preferably in combination with collagenase and, optionally, another hydrolase such as hyaluronidase.

PSA is a proteolytic enzyme, which is one of the most abundant proteins in the prostate secretion. Activated PSA may degrade prostate cancerous tumors by, for example, interfering with the initial growth stage of a tumor and/or interfering with the angiogenesis stage. The initial stage of prostate cancer growth involves the tumor growing to about the size of a pea. The tumor cannot get any larger unless it can form its own blood vessels around and inside the tumor, a process known as angiogenesis. Angiogenesis involves sending chemical signals to surrounding blood vessels that erode the vessel walls, sending capillaries toward the tumor. By interfering with angiogenesis, the tumor cannot grow beyond its initial size. In one aspect, PSA may be activated by administering calcium ions.

In another aspect, a method of treating prostate cancer is directed to administering a composition that includes a therapeutically effective concentration of a collagenase. Collagenase may degrade prostate cancerous tumors by, for example, supporting connective tissue around and inside of the cancerous tumor including angiogenesis-generated capillaries.

In another aspect, a method of the invention is directed to local administration of a therapeutically effective concentration of collagenase in combination with a glycosidase, a protease, a nuclease, a lipase, an esterase, a streptokinase, or a combination thereof. Preferably a glycosidase, such as, for example, hyaluronidase, is administered with collagenase.

Compositions used in methods of the invention may also include or be administered in combination with calcium ions, a nonionic surfactant, such as, for example, Triton® X-100, and an antibiotic, such as, for example, gentamicin.

DETAILED DESCRIPTION OF THE INVENTION

The present invention provides a method for treating prostate cancer. In accordance with the present invention, it has been found that compositions containing at least one hydrolytic enzyme can be used to treat prostate cancer. "Treatment" and "treating" as used herein include preventing, inhibiting, curing, and alleviating prostate cancer or symptoms thereof and preventing or alleviating the metastasis of prostate cancer.

Alleviating prostate cancer includes degrading a prostate tumor, for example, breaking down the structural integrity or connective tissue of a prostate tumor, such that the tumor size is reduced when compared to the tumor size before treatment. Curing prostate cancer includes degrading a prostate tumor such that a tumor cannot be detected after treatment. The tumor may be reduced in size or become undetectable, for example, by atrophying from lack of blood supply or by being attacked or degraded by one or more components administered according to a method of the invention.

Alleviating metastasis of prostate cancer includes reducing the rate at which the prostate cancer spreads to other organs. Preventing metastasis of prostate cancer includes preventing the prostate cancer from spreading outside of the prostate.

A treatment according to the invention may be carried out by administering a therapeutically effective concentration of a composition including collagenase in an amount effective for alleviating, curing, inhibiting, or preventing prostate cancer or preventing or alleviating the metastasis of prostate cancer.

The composition including collagenase is locally administered to the prostate. Local administration includes delivering the composition into or near the prostate and/or cancerous tumor. Local administration further includes surrounding the prostate and/or cancerous tumor with the composition or applying the composition to the surface of the prostate and/or cancerous tumor. Cancerous tumor includes prostate cancer, cancerous cells, and the like.

Another treatment according to the invention may be carried out by activating PSA in vivo. Activating PSA in vivo includes activating PSA, typically the mammal's endogenous PSA, in and/or near the prostate. PSA is a proteolytic enzyme that, upon being activated, can facilitate dissolution or degradation of a prostate tumor. In one embodiment, PSA can be activated by locally administering calcium ions to the prostate.

Although the methods of the invention are not meant to be limited to a single theory, one theory directed to how the methods of the invention treat prostate cancer will be described. In initial stages, a cancerous tumor grows to about the size of a pea. Through angiogenesis the tumor then grows larger (i.e., the tumor grows blood vessels around and inside itself by sending chemical signals to surrounding blood vessels to send capillaries toward the tumor). It is believed that the treatments of the invention interfere with this development.

PSA is a serine protease having a molecular weight of about 33 kilodaltons and is one of the most abundant proteins in the prostate secretion. It is believed that by activating PSA, PSA can partially or completely dissolve or degrade tumor cells in the prostate. This process can be particularly useful at the initial growth stage of a tumor as well as at the angiogenesis stage. PSA can be activated by, for example, administering calcium ions.

Collagenase is a metalloprotease. According to one theory, the activity of collagenase may be increased in the presence of a small amount of proteolytic enzyme—i.e., the amount of proteolytic enzyme present should not be so high that the proteolytic enzyme digests the collagenase to such an extent that the collagenase becomes inactive. PSA secreted into the prostate may be sufficient to increase the activity of collagenase. By increasing the activity of collagenase, the activity of collagenase is raised from a level that may be ineffective for cleaving sufficient substrate (e.g., degrading connective tissue) to a level that may be effective for cleaving sufficient substrate. Then collagenase, in the presence of PSA, for example, can degrade collagen or connective tissue, tumor blood vessels, and/or basement membranes of the tumor cells. As a result, the tumor blood supply is reduced or eliminated, causing the tumor cells to die. This may also result in a person's immune system further attacking the tumor and aiding the alleviation or cure of prostate cancer or the alleviation or prevention of metastasis of prostate cancer.

In methods of the invention, collagenase can also be administered in combination with other proteases, enzymes, or proteins suitable for increasing the activity of collagenase or for aiding in the degradation of a tumor. For example, collagenase can be administered in combination with a protease, a glycosidase, a nuclease, a lipase, an esterase, a streptokinase, or a combination thereof.

Glycosidases include any enzyme that catalyzes the hydrolysis of glycosidic linkages. Suitable examples include hyaluronidase, neuraminidase, amylase, and lysozyme. Preferably the glycosidase includes hyaluronidase.

Proteases include any enzyme that catalyzes the hydrolysis of one or more peptide bonds in a protein or peptide, such as, for example, carboxypeptidases, aminopeptidases, and endopeptidases. More specific suitable examples include elastase, trypsin, chymotrypsin, pronase, dispase, bromelin, clostripain, thermolysin, subtilisin, papain, chymopapain, fibrinolysin, serrathiopeptidase, pancreatin, cathepsin-G, plasminogen activator, and PMN leukocyte serine protease.

Nucleases include any enzyme that catalyzes the hydrolysis of ester linkages in nucleic acids, such as, for example, ribonuclease and deoxyribonuclease. Suitable examples include DNase I and RNase.

Esterases includes any enzyme that catalyzes the hydrolysis of an ester. A suitable example includes cholesterol esterase.

Lipases include any enzyme that catalyzes the hydrolysis of acylglycerol carboxylic esters. A suitable example includes phospholipase.

Streptokinases include proteins that form a complex with plasminogen that then catalyzes the activation of plasminogen to plasmin.

The compositions can also include or be administered in combination with calcium ions, a surfactant, and/or an antibiotic.

The components of the composition—collagenase, additional protease, protein, or enzyme, calcium ions, surfactant, and antibiotic—can be administered alone, sequentially, or preferably, combined with one another in the form of a liquid pharmaceutical unit dosage form suitable for local administration. The dose of the composition administered can vary over a wide range as can readily be determined by the clinician. The preferred dosage for obtaining the desired therapeutic objective can vary depending on the age of the patient, nature and severity of disease, potency of the composition, and route of administration.

Preferably, the compositions suitable for use in methods of the invention include collagenase and at least one of a glycosidase, preferably hyaluronidase; a protease, preferably trypsin, chymotrypsin, pronase, elastase, dispase, or fibrinolysin; or a nuclease, preferably DNase I. More preferably, the compositions include collagenase and a glycosidase, preferably hyaluronidase. Compositions suitable for use in methods of the invention have been described in U.S. Pat. No. 5,116,615 issued to Gokcen et al., incorporated herein by reference.

Collagenase

Bacterial collagenase, for example, *Clostridium hystolyticum*, EC 3.4.24.3, is a well—characterized, commercially—available enzyme that degrades collagen into small peptides by hydrolysis at several sites along the triple helix. Collagenase contains $Zn^{+2}$ in its active site and requires $Ca^{+2}$ for binding to its substrate and for achieving the conformation necessary for full catalytic activity.

Intravenous injections of collagenase have shown a very low degree of danger to experimental animals. In mice the IV LD-50 of crude collagenase has been shown to be 300 mg/kg body weight. Oral solutions of collagenase in water have been proven to be nontoxic at doses as high as 8,000 mg/kg body weight. The acute IV LD-50 in rats has been shown to be 1272 U/kg for collagenase.

Commercial preparations of bacterial collagenase often include small amounts of contaminating proteases, peptidases, mucopolysaccharidases, and glycosidases including: clostripain, trypsin, and a caseinase-like aminopeptidase. Clostripain is the most abundant contaminating enzyme in crude collagenase preparations. Clostripain contains an essential SH group, is activated by cysteine, and is inhibited by sulfhydryl binding agents. Clostripain also has trypsin-like specificity. Crude collagenase preparations with small amounts of contaminating enzymes such as trypsin and clostripain are often more effective than highly purified preparations of collagenase, suggesting that a possible combined action of the multiple enzymes or proteases aids in the treatment of prostate cancer. These enzymes and/or proteases can help activate collagen and/or can help degrade the tumor by catalyzing the hydrolysis of bonds important to the growth or structural integrity of the tumor.

Crude collagenase preparations are especially useful for treatment when combined with other proteins and/or enzymes, such as, for example, a glycosidase, a protease, a nuclease, a lipase, an esterase, a streptokinase, or a combination thereof.

Glycosidases

Examples of glycosidases suitable for use in methods of the invention include hyaluronidase, neuraminidase, lysozyme, and amylase. Preferably the glycosidase is hyaluronidase.

Hyaluronidase (hyaluronate-4-glycanhydrolase) is a known enzyme that catalyzes the degradation of hyaluronic acid (an acidic mucopolysaccharide) into disaccharides, tetrasaccharides, or a mixture of both. Hyaluronidase derived from ovine testes (EC 2.1.1.35) is preferred.

In animals, the intravenous injections of 75,000 International Units of hyaluronidase results in no significant change in blood pressure, respiration, body temperature, or renal function. Hyaluronidase is typically not injected into areas of known infection.

Amylase includes enzymes, such as, for example, α-amylase or β-amylase, able to hydrolyze O-glucosyl linkages in starch, glycogen, and related polysaccharides.

Neuraminidase degrades 2,3-, 2,6-, and 2,8-glucosidic linkages joining terminal nonreducing N- and O-acylneuraminyl residues to galactose, N-acetylhexosamine, or N- or O-acylneuraminyl residues to galactose, N-acetylhexosamine, or N- or O-acylated neuraminyl residues in oligosaccharides, glycoproteins, or glycolipids.

Lysozyme hydrolyzes β-1,4-linkages between N-acetylmuramic acid and 2-acetamido-2-deoxy-D-glucose residues in peptidoglycan heteropolymers. Lysozyme is identified by EC 3.21.17.

Proteases

Examples of proteases suitable for use in methods of the invention include elastase, trypsin, chymotrypsin, pronase, dispase, bromelin, clostripain, thermolysin, subtilisin, papain, chymopapain, fibrinolysin, serrathiopeptidase, pancreatin, cathepsin-G, plasminogen activator, and PMN leukocyte serine protease.

Elastase includes any protease that hydrolyzes elastin. One example is pancreatic elastase identified by EC 3.4.21.36. Pancreatic elastase catalyzes the hydrolysis of proteins, including elastin, with preferential cleavage at Ala-Xaa.

Trypsin is a serine endoprotease that preferentially cleaves at Arg-Xaa and Lys-Xaa. Trypsin is identified by EC 3.4.21.4.

Chymotrypsin is a serine endopeptidase identified by EC 3.4.21.1.

Pronase (a registered trademark of Calbiochem/Behring, La Jolla, Calif.) is a mixture of various exo- and endoproteases, obtained from *Streptomyces*. It is able to hydrolyze virtually any protein almost completely to free amino acids.

Dispase is a neutral metalloprotease typically obtained from *Bacillus polymyxa*.

Bromelin is a cysteine protease that has broad specificity and is identified by EC 3.4.22.32.

Clostripain is a cysteine protease that preferentially cleaves Arg-Xaa and Arg-Pro bonds and is identified by EC 3.4.22.8.

Thermolysin is a metalloendoprotease that preferentially cleaves Xaa-Leu and Xaa-Phe and is characterized as EC 3.4.24.27.

Subtilisin is a serine endoprotease that catalyzes the hydrolysis of proteins with broad specificity for peptide bonds and is identified by EC 3.4.21.62.

Papain is a cysteine endopeptidase that preferentially hydrolyzes peptide bonds at the carbonyl end of Arg, Lys, Phe residues and is identified by EC 3.4.22.2. Papain also has esterase, thioesterase, transamidase, and transesterase activity.

Chymopapain is an endoprotease with specificity similar to that of papain. Chymopapain is identified by EC 3.4.22.6.

Fibrinolysin is also known as plasmin, which is a serine protease that converts insoluble fibrin of a blood clot into soluble products. It is formed from plasminogen by proteolysis and preferentially cleaves Lys-Xaa and Arg-Xaa. Fibrinolysin is identified by EC 3.4.21.7.

Cathepsin G is a glycoprotein serine endoprotease with a specificity similar to that of chymotrypsin. This protease is identified by EC 3.4.21.20.

Plasminogen activators include any serine protease that converts plasminogen into plasmin.

PMN leukocyte serine protease includes a serine protease found in PMN leukocytes.

Other proteases include but are not limited to pancreatin and serrathiopeptidase.

Nucleases, Esterases, and Lipases

Examples of nucleases suitable for use in methods of the invention include DNase I and RNase. DNase I (Deoxyribonuclease I) is an enzyme that catalyzes the endonucleolytic cleavage of DNA into 5'-phosphodinucleotide and 5'-phosphooligonuleotide end products. DNase I is identified by EC 3.1.21.1. RNase is any of a group of nuclease enzymes that cleave phosphodiester bonds and chains of RNA.

Examples of esterases suitable for use in methods of the invention include cholesterol esterase.

Examples of lipases suitable for use in methods of the invention include phospholipase. Phospholipase is an enzyme that catalyzes the hydrolysis of a glycerophospholipid. Phospholipases have been subdivided into types $A_1$, $A_2$, B, C, and D.

Calcium Ions

Calcium ions can also be administered to treat prostate cancer. Calcium ions can serve to activate both collagenase and/or PSA. The calcium ions can be provided by, for example, calcium chloride. The concentration of calcium ions is typically between about 1 mM and 50 mM, preferably between about 10 mM and 50 mM, and more preferably about 20 mM.

According to one treatment, activated PSA can degrade or dissolve a prostate tumor and interfere with initial tumor growth and/or angiogenesis. According to another treatment, collagenase can be administered in combination with PSA being activated, and the activated PSA can increase the proteolytic activity of collagenase. Collagenase can, in turn, degrade a prostate tumor. According to another treatment, collagenase can be administered in combination with calcium ions and/or a protease, an enzyme, a protein, a nonionic surfactant, or an antibiotic to treat prostate cancer.

Nonionic Surfactants

Compositions suitable for use in methods of the present invention also can include or be administered in combination with a nonionic surfactant. A surfactant aids in the solubilization and lysis of prostatic cancer tissue. Examples of suitable surfactants include alkylphenylpolyoxethylene surfactants such as Triton® X-100 (octylphenoxypolyethoxyethanol, which is an octylphenylpolyoxyethylene oxide available from Rohm and Haas, Philadelphia, Pa.) and other polyoxyalkylene-based nonionic surfactants such as Tween® 20/80 (Atlas Chemical), Genapol X-080/100/150, C-100 (Hoechst AG), Thesit (Destin-Werk GMBH), Brij 35, Lubrol PX (ICI Americas), Pluronic F-127 (Wyandotte Chemicals Corp.), Nonidet P-20/40 (Shell Oil Corp.), Igepal CO-630/710 (GAF), Surfonic N-95 (Jefferson), Tergitol NP-27 (Union Carbide). Other suitable surfactants include the condensation products of ethylene oxide with partial fatty acid esters of sorbitol and sorbitol anhydride, such as, for example, the Tween® series (Atlas Chemical) wherein the molar ratio of ethylene oxide to alcohol is within the range of about 15:1 to 25:1 with the fatty acid component comprised of laurate, stearate, or oleate ($C_{10}$–$C_{20}$).

Other nonionic surfactants that can be employed in the present composition include the ethylene oxide esters of $C_6$–$C_{12}$ alkyl phenols such as nonylphenoxy polyoxyethylene ether. Particularly useful are the esters prepared by condensing 8 to 12 moles of ethylene oxide with nonylphenol. Commercially available detergents of this type include the Igepal CO series (GAF Corp.).

Additional useful nonionic surfactants can include the condensation products of ethylene oxide with a hydrophobic polyoxyalkylene base such as propylene oxide condensed with propylene glycol. Compounds of this type include the commercially available surfactants Pluronic F-127, Pluronic PX, and Pluronic L-62 (Wyandotte Corp.).

Further useful nonionic surfactants include the condensation products of $C_8$–$C_{22}$ alkyl alcohols containing 2 to 50 moles of ethylene oxide per mole of alcohol. Detergents of this type include the condensation products of $C_{10}$–$C_{20}$ fatty alkyl alcohols containing 3 to 45 moles of ethylene oxide per mole of alcohol. These compounds are commercially available as the Poly-Tergent SLF series (Olin Chemicals) or the Tergitol series (Union Carbide).

The performance of suitable surfactants can be effected by, for example, pH, temperature, ionic strength, and surfactant concentration.

Surfactants are preferably added to the present composition at a concentration of about 0.1% to 10% by volume of the composition. More preferably, the surfactants are present at a concentration of about 0.5% to 5% by volume.

Antibiotics

Compositions suitable for use in methods of the invention also can include or be administered in combination with an antibiotic. Local administration to the prostate, such as by, for example, direct injection of the prostate, is generally a safe, simple, and effective means of introducing the composition into the body. Yet some local administration techniques can be associated with the risk of acquiring bacterial infection that can lead to, for example, fever, bacteriuria, and bacteremia.

Antibiotics usually relieve the symptoms of acute prostatic infections promptly. However, no antimicrobial agent is effective against all pathogenic urinary tract microorganisms. Each has its own spectrum of activity against one or a variety of species. The therapeutic agents for curing bacterial prostatitis preferably are highly lipid soluble; possess basic pKa; show minimal binding to plasma proteins; and are bactericidal against the common gram negative uropathogens.

It is preferred that the present enzyme composition include a suitable antimicrobial agent to prevent or reduce the incidence of bacterial infection that can be associated with the present injection method. Antibiotics used typically provide adequate protection against the commonly encountered bacterial strains of uropathogens including: *Escherichia coli, Streptococcus faecalis, Proteus/Pseudomonas* spp., and coagulase-positive *Staphylococcus*. The antibiotic is preferably selected to not substantially inhibit the enzymatic activity of the composition.

The antibiotics of the present claimed composition, preferably gentamicin or trimethoprim/sulfamethoxazole, can be selected from the groups of antibiotics that exhibit the appropriate spectrum of activity against the commonly encountered bacterial strains of uropathogens including: penicillins (penicillin G, penicillin V, benzathine penicillin); amino penicillins (ampicillin, amoxicillin); carboxy penicillins (carbenicillin, piperacillin, mezlocillin); penicillinase resistant penicillins (methicillin, oxacillin, nafcillin); cephalosporins (cephalexin, cephalothin, cefotaxime, cephazolin); aminoglycosides (streptomycin, neomycin, kanamycin, tobramycin, amikacin, netilmicin, sisomicin); tetracyclines (doxycycline, minocycline, tetracycline), polymyxins (polymyxin B & E); sulfonamides (sulfisoxazole, sulfasuxidine); fluoroquinolones(ciprofloxacin, norfloxalin); basic macrolides (erythromycin, oleandomycin); lincomycin; clindamycin; chloramphenicol; nitrofurantoin; and nalidixic acid.

Examples of antibiotics suitable for use in methods of the invention include gentamicin sulfate (Garamicin®, Schering Corp., Kenilworth, N.J.), trimethoprim/sulfamethoxazole (Septra®, Burroughs Wellcome, Research Triangle Park, N.C.), nitrofurantoin, nalidixic acid, tobramycin, amikacin, and netilmicin sulfate.

Preferably gentamicin sulfate or trimethoprim/sulfamethoxazole are administered. The administration of trimethoprim/sulfamethoxazole currently is the drug of first choice in the treatment of bacterial prostatitis. Recent studies have indicated that a single dose of gentarnicin, trimethoprim/sulfamethoxazole, or netilmicin sulfate is as effective as longer treatment in the prevention of postoperative bacterial urinary tract infections.

Trimethoprim is a lipid-soluble base with limited binding to plasma proteins, and typically shows prostatic tissue: serum levels of 2:1 to 3:1. Trimethoprirn/sulfamethoxazole (TMP/SMX) produces therapeutic levels in the urine and prostatic secretions with an appropriate antibacterial spectrum of activity. Recommended therapy with TMP/SMX involves dosages of 160 mg TMP and 800 mg SMX, orally twice a day for 30 days. Should TMP/SMX not be tolerated (allergies), gentamicin therapy is recommended.

The antibiotic generally is present in the composition at a concentration of about 0.15 to 150 µg/ml. The preferred antibiotic, gentamicin sulfate, is present in the composition at a concentration of 1.5 to 150 µg/ml, preferably 10 to 25 µg/ml. Alternatively, for those patients who may be allergic to aminoglycosides in general, and gentamicin in particular, the combination drug trimethoprim/sulfamethoxazole can replace gentamicin as the preferred antibiotic of the present claimed composition. Trimethoprim is preferably present at a concentration of 1 to 10 μg/ml, more preferably 5 to 10 μg/ml. Sulfamethoxazole is preferably present at a concentration of 30 to 105 μg/ml, more preferably 50 to 105 μg/ml.
Preparation and Testing of an Illustrated Composition The present invention discloses as a preferred embodiment an aqueous composition containing a safe and therapeutically effective concentration of the hydrolytic enzymes collagenase and hyaluronidase, the detergent Triton® X-100, and the antibiotic gentamicin for local administration. It is preferred that the disclosed composition be prepared as a relatively concentrated solution of hydrolytic enzymes in a relatively small volume.

It is preferable that the claimed composition be provided in a unit dosage form suitable for intraprostatic injection. The composition can be administered to the patient as an injectable dosage of a solution or suspension of the compounds in a physiologically acceptable liquid diluent, such as pyrogen-free saline. For example, vials containing a lyophilisate of the composition can be prepared such that a sterile aliquot of the composition can be reconstituted and withdrawn as a pharmaceutically acceptable aqueous solution for injection into living mammals. A preferred unit dose contains 250 to 250,000 U/ml collagenase; 160 to 160,000 U/ml hyaluronidase; 0.1% to 10% nonionic surfactant; and 0.15 to 150 μg/ml antibiotic. More preferably a unit dose contains 2,500 to 25,000 U/ml of collagenase; 1,600 to 16,000 U/ml of hyaluronidase; 0.5 to 5% nonionic surfactant; and 15 to 150 μg/ml antibiotic.

Compositions of the present invention were prepared. Collagenase (Sigma Chemical Co., St. Louis, Mo.) and hyaluronidase (Boehringer/Mannheim Corp., Indianapolis, Ind.) were obtained as lyophilisates and reconstituted with citrate-buffered saline containing 20 mM to 50 mM $CaCl_2$ (CBSCa) to the desired concentration. Collagenase, obtained from *Clostridium hystolyticum*, was chromatographically purified and contained small contaminating amounts of the enzymes clostripain, trypsin, and caseinase. Hyaluronidase, obtained from ovine testes, was also purified chromatographically. All enzyme activities were expressed as international units per mg.

The enzymes are stable when stored as lyophilisates at 4° C. However, it is advantageous to prevent access of moisture to lyophilized enzymes. For example, cold vials of lyophilized enzyme are typically first be warmed to room temperature before being opened. Dilute reconstituted solutions of enzymes are typically stored at 4° C., protected from light, and placed in an ice-bath when working at the bench.

Freshly distilled, deionized, sterile water is preferred for the reconstitution of enzymes and preparation of buffers used for injectable solutions. In the preferred embodiment, the buffer solution used is 0.05 M citrate-buffered saline (CBS, pH 6.7), containing an adequate amount (preferably 0.01 M to 0.05 M, more preferably 0.02 M to 0.05 M) of calcium ions to activate the collagenase. It is recognized that any suitable buffer solution such as Ringers saline or tris-buffered saline can be used. However, the buffer typically contains sufficient calcium ions to activate collagenase, and typically does not contain calcium chelators such as EDTA or other inhibitors of enzyme activity such as cysteine.

A preferred buffer exhibits a physiological pH, which can range from about 6.5 to 7.5, with pH 6.7 to 7.0 preferred. The saline, e.g., sodium chloride, concentration is preferably about 0.1 M to 0.2 M with about 0.15 M to 0.2 M most preferred. Similarly, the concentration of citrate is preferably about 0.02 M to 0.1 M with 0.05 M to 0.1 M most preferred.

A preparation of 0.05 M CBS+20 mM $CaCl_2$ (pH 6.7) is composed of 550 mg sodium citrate, 190 mg NaOH, and 876 mg NaCl dissolved in 100 ml sterile, pyrogen-free, deionized $H_2O$. The solution was adjusted to a pH of 6.7 with 3 ml of 1 N NaOH, and 294 mg $CaCl_2$ was added. The surfactant Triton® X-100 (Malinckrodt, Paris, Ky.) and the antibiotic gentamicin (Sigma Chemical Co.) were added to obtain appropriate final concentrations. Triton® X-100 exhibits a density of 1.082 g/ml at 20° C. (924 Tl/g at 20° C.). Gentamicin is included so as to obtain a final concentration of 150 μg/ml by adding 1.5 ml of a 10 mg/ml (15 mg) sterile solution of the antibiotic to 100 ml of the mixture.

The resulting solution can be purified and sterilized by standard techniques. A solution (5 ml) of the enzymes collagenase and hyaluronidase (0.1% to 10%) in citrate buffered saline (pH 6.7) containing Triton® X-100 (0.1% to 10%), the antibiotic gentamicin (1.5 to 150 μg/ml), and $CaCl_2$ (20 mM) is prepared in pyrogen-free water, and passed over a 1 ml column (Detoxi-Gel®) to remove potential endotoxins. The final step in the preparation of a pharmaceutically acceptable solution involves the passage of the composition through a certified sterile, nonpyrogenic microporous polysulfone filter with a pore size of 0.2 micrometer. Low protein binding filter membranes composed of polysulfones show significantly less protein absorption than comparable cellulose acetate/nitrate membrane filters. Filtration through a 0.2 mm sterile filter affords protection against contamination with microorganisms. Additionally, filtration minimizes the risks to patients posed by insoluble particulates or microaggregates.

Reconstitution and preparation of pharmaceutically acceptable solutions for parenteral use in humans is performed routinely in hospital pharmacies as standard practice. Solutions of collagenase/hyaluronidase/Triton® X-100/gentamicin (CHTG) in 0.05 M citrate-buffered saline containing 20 mM $CaCl_2$ (CBSCa 6.7) ranging in concentration from 0.1% to 10% are stable for 2 weeks when stored at 4° C. and remain highly effective in solubilizing human and canine prostatic tissue. The toxicity of the composition is not believed greater than the toxicities of the individual components, which are known.

Collagenase (EC 3.4.24.3) derived from *Clostridium hystolyticum* was purchased from Sigma Chemical Company (Type XI, Product#C-7657, Lot Numbers: 96F-6801 and 96F-6838; Type XI-S, Product #C-4785, Lot Number: 17F-6814). Lot to lot variations of enzyme activity in terms of collagenase U/mg and levels of contaminating enzymes were observed and ranged from: 1910 to 2450 U/mg collagenase, 0.86 to 1.4 U/mg clostripain, 40 to 85 U/mg caseinase, and 0.05 to 0.52 U/mg trypsin.

One unit of collagenase activity is defined as the amount of collagenase that will release peptides from native collagen, equivalent in ninhydrin color, to 1 micromole of L-leucine in five hours at pH 7.4 at 37° C. in the presence of calcium ions. One unit of clostripain will hydrolyze 1 micromole of N-alpha-benzoyl-L-arginine ethyl ester (BAEE) per minute at pH 7.6 at 25° C. in the presence of 2.5 mM dithiothreitol. One unit of caseinase (nonspecific protease) will hydrolyze casein to produce color equivalent to 1 micromole (181 Tg) of L-tyrosine in five hours at pH 7.5 and 37° C. (color by Folin-Ciocalteu reagent). One unit of trypsin activity will hydrolyze 1 micromole of N-alpha-benzoyl-L-arginine ethyl ester (BAEE) per minute at pH 7.6 and 37° C.

The activities of collagenase and any additional enzymes can be determined according to methods known in the art. Examples of collagenase and hyaluronidase assays are disclosed in U.S. Pat. No. 5,116,615 issued to Gokcen et al., incorporated herein by reference.

Compositions are essentially free of endotoxins, which are pyrogenic lipopolysaccharide components of gram-negative bacteria that are known to have potent adverse effects in humans and animals.

Methods of Delivery

One method of the invention is directed to activating PSA in vivo. In one embodiment, PSA can be activated in vivo by, for example, locally administering a therapeutically effective concentration of calcium ions. PSA can be activated in vivo in combination with locally administering a therapeutically effective amount of collagenase, which can be administered in combination with a selected protease, protein, or enzyme, calcium ions, a surfactant, and/or an antibiotic.

Another method of the invention is directed to administering an aqueous parenteral composition suitable for treating prostate cancer. Suitable compositions are described above and include a therapeutically effective amount of collagenase and optionally include one or more of the following: an above-identified selected protease, protein, or enzyme, calcium ions, a surfactant, and an antibiotic. In a preferred embodiment, the composition includes collagenase, hyaluronidase, calcium ions, a surfactant, and an antibiotic. The calcium ions can be supplied by, for example, $CaCl_2$. The surfactant can be, for example, Triton® X-100, and the antibiotic can be, for example, gentamicin.

The composition is locally administered to the prostate. Local administration includes delivering the composition into or near the prostate and/or cancerous cells or tumor, preferably into the tumor. Local administration also includes surrounding the prostate and/or cancerous tumor with the composition or applying the composition to the surface of the prostate and/or cancerous tumor. For example, the composition can be locally administered by direct intraprostatic injection or by infusion into the prostate. Small volumes, such as, for example, about 5 cc or less, are preferably injected. Larger volumes, such as, for example, greater than about 5 cc, are preferably transfused slowly over, for example, about 15 to 20 minutes.

To verify the accuracy of the administration—i.e., whether the composition is administered near or into the cancerous cells or tumor—the urologist typically has a good mapping of the prostate from, for example, ultrasonic imaging, which can be obtained during the diagnostic work-up and prostate biopsy.

The composition is typically administered such that local administration of therapeutically effective amounts of the composition result in treating prostate cancer. Preferably the amount is effective to degrade the prostate tumor, either curing or alleviating prostate cancer.

In one embodiment, the composition is locally administered by intraprostatic injections. Intraprostatic injections are carried out by inserting a long, fine needle into the prostate under digital rectal control and/or ultrasonic guidance. The injections are usually done under local anesthesia, and the injection solution can be diluted with iodocaine. During the injection, the needle can be frequently relocated in order to obtain the best possible distribution of the composition. Several routes of injection are available for the introduction of the disclosed composition to the prostate.

The preferred route of administration is by means of transurethral intraprostatic (intralesional) injection. The transurethral technique is immediately preceded by catheterization. The volume of the composition injected typically varies from 1 to 50 cc.

To optimize the effectiveness of the injected composition, it can be desirable to dilate the prostatic urethra with an inflatable balloon. The cystoscopically inserted balloon inhibits the immediate egress of the injected enzyme solution through the porous duct system that empties into the urethra. The advantage of this route of injection is that the method allows for direct cystoscopic visualization of the nodular areas of pathology and for the placement of a high concentration of the composition at the desired location without the risk of metabolic inactivation. The pain and discomfort experienced by patients during direct injection of the prostate typically are minimal and comparable to intramuscular injections.

Alternatively, the transperineal or transrectal routes of prostatic injection can be used. The transperineal route of injection involves the placement of 22 g×20 cm aspiration biopsy needle through the perineum into the prostate guided by ultrasound and/or digital palpation. Again, 1 to 50 cc of the disclosed composition is typically injected into each lateral lobe of the prostate. The injections are generally done under local anesthesia. During injection, the needle is frequently relocated to obtain the best possible distribution of the composition. The position of the needle can be guided by ultrasound while kept under constant digital rectal control. The transperineal route of injection can be a better alternative than either the transurethral or transrectal routes in terms of reducing potential complications due to postinjection bacterial infection.

To reduce the incidence of bacterial infection that can be associated with transperineal intraprostatic injection, aseptic injection techniques are recommended and are well known to those skilled in the art. Any one of a variety of standard bactericidal preparations such as Phiso-Hex®, Betadine®, povidone-iodine, or chlorhexidine applied to the skin of the perineum provides adequate pre-injection antibacterial protection. With sterile urine, adequate skin preparation, and sterile technique, the entire procedure should have a low rate of infectious complication.

The transrectal route allows needle introduction through the rectal wall and injection of the prostate while performing digital rectal palpation. Injection via the transrectal route is performed with a slightly curved 22 g×20 cm flexible aspiration biopsy needle. The use of a Franzen needle guide (Precision Dynamics, San Fernando, Calif.) allows the needle to be safely directed into a suspected lesion under ultrasonic and/or tactile guidance techniques. The sterilized prostate needle guide is placed on a gloved index finger. A finger cot is placed over the needle guide. The index finger and needle guide are inserted into the rectum and suspected lesions of the prostate are palpated. The needle is inserted through the guide and advanced into the tissue. Approximately 1 to 50 cc of the solution can be injected into the lateral lobes of the prostate. In order to inject sufficient material, the needle can be moved back and forth three to five times. An anesthetic jelly can be applied before injection to reduce pain during needle puncture.

Upon injection, the prostatic lobe swells, increases in size, and becomes turgid. Injected fluid forced through the veins at the site of injection can induce wide spread venospasm associated with microinfarcts. Acute urinary retention can occur in the immediate post injection period. Fluid injected into the prostate fills the alveoli of the gland at the site of injection and can rupture through the walls of adjacent alveoli entering the prostatic urethra via the alveolar ducts. As much as ⅓ to ½ of the injected fluid can ultimately reach the prostatic urethra.

A bolus injection of more than 5 cc of the composition into the body of the in situ prostate can result in reflexive smooth muscle contraction causing the therapeutic enzyme solution to be rapidly emptied through the porous ducts, away from the target tissue, and into the urethra. The force of the injection can cause rupture of prostatic tissue at the site of injection. The injected fluid can gain access to the ducts of the glandular alveolar system and completely fill the gland. Once the gland is filled, the fluid takes the path of least resistance and flows to the urethra.

Injection fluid can gain access to the prostatic circulation and be responsible for scattered minute areas of infarction. Enzyme induced thrombophlebitis of the veins can be responsible for the appearance of widespread hemorrhagic infarctions. About ⅕ of the prostatic injection fluid can enter the general circulation as demonstrated by experiments involving excretion of methylene blue by the kidneys. The subcapsular and periurethral zones of the prostate are more vascular in nature and can enhance the flow of the fluid into the blood stream. Injections of India ink carbon particles into the prostate resulted in no gross or microscopically detectable particles in the lymphatics of the pelvis. Prostatic injection fluid can also reach the surface of the prostate and periprostatic tissue through the point of needle entry.

Radiographs taken immediately after intraprostatic injection of radio-opaque microemulsions of barium sulfate have shown fluid leakage beneath the prostatic capsule and escape into the bladder. Occasionally, the fluid has been seen to leak outside the capsule as well.

The injected lobule of the prostate undergoes necrosis mainly due to the enzymatic action of the injected composition and partly due to the shear force of the fluid injected under pressure. Part of the fluid that leaks back through the point of needle entry can cause thrombosis of surface vessels and be responsible for adhesions with adjacent viscera. The quantity of fluid that leaks back depends upon the local pressure and is likely to increase with the force of the injection. Injected fluid passing through the periurethral veins can cause their inflammation and thrombosis, which in turn can result in necrosis and sloughing of the urethral epithelium.

Urethral and periurethral solubilization is expected to occur around the entire circumference of the prostatic urethra which can lead to denudation of the urethral epithelium. Histopathologic changes associated with injection of the tissue solubilizing enzymes include those due to fluid escape along ducts of the gland resulting in damage to the ducts and surrounding alveoli. The fluid that leaks back through the point of needle entry can affect the capsular vessels and smooth muscle fibromuscular stroma situated there.

Direct localized injection of the prostate results in a high concentration of therapeutic enzymes at the very focus of the problem without the risk of metabolic inactivation. However, intraprostatic injections during acute exacerbations of infection are not recommended because of the danger of general dissemination of the infection and possible septicemia. Hematuria and hemospermia can be present for some weeks following the injection.

Depending upon the patient being treated, the therapeutically effective dose of the composition administered can range from 1 cc to 50 cc preferably containing 160 to 160,000 U/ml hyaluronidase; 250 to 250,000 U/ml collagenase; 0.1 to 10% nonionic surfactant preferably Triton® X-100; and 0.15 to 150 µg/ml antibiotic, preferably gentamicin. More preferably, a dose includes 2,500 to 25,000 U/ml collagenase; 1,600 to 16,000 U/ml hyaluronidase; 0.5 to 5% nonionic surfactant, preferably Triton® X-100; and 15 to 150 µg/ml antibiotic, preferably gentamicin. These dosage ranges represent quantities of the various components of the composition that are estimated to be therapeutically effective for treating prostate cancer. But the dose of the composition can vary depending on the age of the patient, nature and severity of disease, potency of the composition, and route of administration. Treatment regimens encompassed by a preferred embodiment of the present invention employ the intraprostatic injection of safe and effective amounts of the preferred composition to cause the regression of prostate cancer. The injections can be administered in daily, weekly, or monthly injection protocols until the therapeutically desired result is obtained.

In some embodiments, to determine the appropriate dosage, the size of the tumor is estimated because a larger tumor can require a higher concentration of the composition suitable for use in methods of the invention. For example, for a tumor smaller than 7 g, a single bolus dose of the composition is typically administered. A bolus dose can be 5 cc and preferably contains 250–250,000 U/ml collagenase, 160–160,000 U/ml hyaluronidase, 0.1% to 10% nonionic surfactant, 0.15 to 150 µg/ml antibiotic, and 20 mM to 50 mM $CaCl_2$ in citrate buffer (pH 6.7). The bolus dose is preferably injected slowly into the tumor, for example, over several minutes. This injection can be followed by additional injections if necessary. For example, this treatment can be administered again in, for example, a week or a month or can be administered repeatedly, for example, weekly or monthly.

For a tumor between 7 and 15 g, a first bolus dose is typically followed by a larger dose of the composition. For example, the 5 cc bolus dose described above is first administered. Then, a second dose of the same composition in 25 to 45 cc is slowly administered over, for example, about 15 to 20 minutes. These injections can be succeeded by still another dose if necessary, but a total volume of 50 cc for all doses is typically not exceeded. For example, this treatment can be administered again in, for example, a week or a month or can be administered repeatedly, for example, weekly or monthly.

For a tumor larger than 15 g, a dose of up to about 50 cc can be administered by first administering a bolus dose followed by a larger dose as described above.

Other Methods of Delivery

If problems are encountered that limit or inhibit the therapeutic effects of the present composition, alternative means of delivery can be used. For instance, the effectiveness of enzyme therapy can be limited by the short circulating half-lives of exogenously administered enzymes, by the development of immunological responses to foreign protein, by inhibition from antiproteinase effectors (I-1-antitrypsin, I-2-macroglobulin), or by the inability to specifically target the enzymes to nodular areas of pathology.

A number of different carrier systems can be utilized to carry the enzymatic composition to the desired site in the prostate. In general, a suitable carrier guides the therapeutic agent to its target without loss of specificity or reactivity. The carrier is preferably capable of linkage with the therapeutic enzymes and remaining as a complex until delivery is completed. The carrier preferably avoids triggering the immune defense mechanisms resulting in biodegradation or inactivation of the present composition.

The composition can be administered as a depot formulation that permits sustained release, prevents access to general circulation, and increases the prostate-specific localization of the composition. Such a formulation can be provided as a slow-release implant or can be microencapsulated or attached to a biodegradable polymer or a prostate-specific iumunoglobulin.

The use of antibodies as an enzyme composition carrier system can be desirable. The use of antibodies as carrier systems for the delivery of therapeutic agents to specific tissues exploits the antibody's unique ability to recognize and bind to targeted antigens. Also, antibodies carrying therapeutic reagents can be more effectively localized in tissues that are highly vascular in nature or are undergoing neovascularization. Additionally, cocktails of immuno-enzyme conjugates recognizing different cell types with different specificities can be useful.

Tissue-specific monoclonal antibodies can be produced that better define the antigenic cellular targets to be localized. The use of F(ab) or F(ab')$^2$ fragments can improve localization properties. Antibodies containing the F(c) fragment tend to be specifically localized over a longer time period than F(ab) or F(ab')$^2$ fragments that exhibit accelerated clearance mechanisms. The recent development of human-mouse (chimeric) monoclonal antibodies can have therapeutic applications and provide advantages over conventional monoclonal antibodies of murine derivation. Human-mouse antibodies exhibit a wide range and high degree of specificity. Chimeric antibodies are less likely than conventional mouse monoclonal antibodies to elicit an immune reaction when injected into humans. The preparation and use of human monoclonal antibodies as carriers can further reduce the degree of immune response in the recipient to the introduction of foreign proteins. The antiglobulin response can also be controlled by such factors as method of antibody preparation, dosage, and route of injection.

The purpose of immuno-targeted enzyme therapy is to deliver an effective concentration of enzymes to a tissue specific site of activity, reduce toxicity to nearby normal tissues, and thereby increase the therapeutic index. Enzymes can be coupled to monoclonal antibodies that bind the enzyme covalently yet do not affect the enzyme's catalytic activity. Enzymes that are coupled to tissue specific monoclonal antibodies can be able to achieve a higher degree of specific localization in the targeted tissue than native enzymes while maintaining their proteolytic activity.

Other specific localization concepts include zymogen-antibody conjugates (trypsinogen) or enzyme-antibody conjugates (collagenase, hyaluronidase, elastase, DNase) that retain both enzyme and antibody activity. Enzymes can be encapsulated in lipoprotein, red blood cell (RBC) ghosts, polylactic acid, and other biodegradable membranes or synthetic microcapsules containing prostate-specific antibodies to increase and maintain specific targeting, localization, and activity of the solubilizing proteases in prostatic tissue.

The administration of collagenase and hyaluronidase can have immunologic consequences as repeated injections can result in the development of antibody titers and the accompanying risk of anaphylaxis or other less serious hypersensitivity reactions. Additionally, the presence of specific antibodies to collagenase or hyaluronidase can inhibit enzyme activity. Potential immunologic problems could occur if the active enzyme is recognized as foreign by the recipient's immune system. Antibodies can be produced against the enzymes and inactivate or precipitate the enzyme. Use of enzymes of human origin or those produced by recombinant techniques can minimize these potential immunologic complications.

Strategies that avoid the immune surveillance system involve methods of entrapment of enzyme preparations in biodegradable vesicles that protect the enzyme activity yet facilitate specific delivery. Targeting to specific sites of cellular pathology can be accomplished by attaching tissue specific proteins (monoclonal antibodies) to these vesicles. Enzymes can also be encapsulated in liposomes or other biodegradable microcapsules and subsequently attached to tissue-specific monoclonal antibodies for specific localization purposes.

Liposomes are small spheres of concentric phospholipid bilayers containing an aqueous phase that have been shown to be useful as carrier systems. Current liposome preparation techniques permit the incorporation of a variety of drugs, hormones, or enzymes into either phase. Monoclonal antibodies can be incorporated into the outer layers of liposomes and provide increased specificity of delivery for the liposome-contained therapeutic agent.

The entrapment of enzymes in synthetic microcapsules or biodegradable vesicles can provide a valuable method of specific delivery in addition to protecting the enzyme from physiologic inactivation and preventing immune complications. Various forms of membrane encapsulation techniques are available for the entrapment of enzymes including: erythrocyte ghosts; synthetic polymeric microcapsules; and lipid vesicles (liposomes) composed of cholesterol, lecithin, and phosphatidic acid. Use of the recipient's own erythrocytes to deliver active enzyme can avoid the potential immunologic and physiologic problems resulting from enzyme administration in synthetic carriers (e.g., liposomes and microcapsules).

The covalent attachment of polyethylene glycol (PEG) to enzymes renders these proteins nonimmunogenic, can extend their circulating half-life, provides a means of escape from inhibition by naturally occurring enzyme inhibitors, and can result in enhanced enzyme activity with decreased autodigestion. The attachment of PEG to proteins is simple and yields homogeneous reaction products that can be purified by ultrafiltration.

The invention is further elaborated by the representative examples that follow. Such examples are not meant to be limiting.

EXAMPLES

Example 1

A First Case Study of a Man with Localized Prostate Cancer

A 70-year-old male is diagnosed with localized prostate cancer (i.e., no metastasis can be detected by means of radionucleid scan and CAT scans). The estimated size of the tumor in the prostate is 7 grams. The location of the tumor is in the right lateral lobe as seen in the sonogram. The PSA level in the blood is 40 ng/ml.

The composition for injection was prepared as previously described (Preparation and Testing of Composition), and contained 12,500 U/ml collagenase; 7,500 U/ml hyaluronidase; 1%(v/v) Triton® X-100; 150 Tg/ml gentamicin; and 40 mmol $CaCl_2$ in 0.05 M citrated-buffered saline (Ph 6.7). The final composition is drawn into a syringe ready for injection (5 cc).

The patient is prepared for a cystoscopy procedure using local anesthesia. A cystoscope is placed into the urethra and the injection needle is inserted into the lesion (the tumor) and is monitored by the ultrasound imaging. Once the needle is secured, 5 cc of the injectable composition is given slowly over a period of about 4 to 5 minutes. During the injection, vital signs are monitored for symptoms of toxic, allergic, or other adverse reactions.

The patient's recovery is normal, and no signs or symptoms of any adverse reactions to the injected composition are observed. The clinical progress is uneventful. The blood PSA level gradually declines over a period of three months to normal levels (4 ng/ml or less) and remains normal. After 5 years, the patient is diagnosed as free of prostate cancer.

Example 2

A Second Case Study of a Man with Localized Prostate Cancer

A 65-year-old male is diagnosed with localized prostate cancer (i.e., no metastasis can be detected by means of radionucleid scan and CAT scans). The estimated size of the tumor is 15 grams and the total prostate weight is 90 grams. The PSA level in the blood is 200 ng/ml. The tumor is located in the right lobe and is one solid nodule.

The composition for injection is prepared as previously described (Preparation and Testing of Composition). It contained 2,400 U/ml collagenase; 1,600 U/ml hyaluronidase; 1%(v/v) Triton® X-100; 150 Tg/ml gentamicin; and 120 mmole $CaCl_2$ in 0.05 M citrate-buffered saline (pH 6.7). The total volume of injection is 30 cc.

Under the guidance of a cystoscope, the composition is injected into the tumor. First, the bolus dose of 5 cc is injected slowly. Next, the remaining 25 cc volume is infused slowly over a period of about 15 to 20 minutes. Upon completion of injection, vital signs are monitored for symptoms of toxic, allergic, or other adverse reactions.

The patient's recovery and the postinjection progress is uneventful. The blood PSA level gradually declines to normal levels (4 ng/ml or less) over a period of three months and remains normal. After 5 years, the patient is diagnosed as free of prostate cancer.

Example 3

A Third Case Study of a Man with Localized Prostate Cancer

A 72-year-old male is diagnosed with localized prostate cancer (i.e., no metastasis can be detected by means of radionucleid scan and CAT scans). The estimated size of the tumor is about 9 grams, and the distribution is rather diffuse. The PSA level in the blood is 30 ng/ml.

A composition including 50 mM calcium-chloride in 0.05 M citrate-buffered saline (pH 6.7) is prepared in a volume of 10 cc. Under the guidance of a cystoscope, the calcium-chloride composition is injected into multiple sites of the prostate. Upon completion of the injection, vital signs are monitored for symptoms of toxic, allergic, or other adverse reactions. Approximately one month later, about 75% of the tumor mass has been degraded. Subsequently, a second injection of 25 mM calcium chloride in 0.05 M citrate-buffered saline is administered intralesionally in a volume of about 5 cc. After three years, the patient is clinically free of cancer, and the patient's PSA levels are within normal limits.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

The invention has been described with reference to various specific and preferred embodiments and techniques. It should be understood, however, that many variations and modifications can be made while remaining within the spirit and scope of the invention.

I claim:

1. A method of degrading a prostate tumor in a mammal comprising local administration to the prostate of a composition comprising therapeutically effective concentrations of collagenase, hyaluronidase, and calcium ions.

2. The method of claim 1, wherein the composition comprises about 1 mM to about 50 mM calcium ions.

3. The method of claim 1, wherein the calcium ions comprise a calcium salt.

4. The method of claim 3, wherein the calcium salt comprises calcium chloride.

5. The method of claim 1, wherein the composition comprises about 1 mM to about 50 mM calcium ions, about 250 to about 250,000 U/ml collagenase and about 160 to about 160,000 U/ml hyaluronidase.

6. The method of claim 1, wherein the composition further comprises an effective concentration of a nonionic surfactant.

7. The method of claim 6, wherein the nonionic surfactant comprises octylphenoxypolyethoxyethanol.

8. The method of claim 1, wherein the composition further comprises an effective concentration of an antibiotic.

9. The method of claim 8, wherein the antibiotic comprises gentamicin sulfate.

10. The method of claim 1, wherein local administration comprises intraprostatic injection.

11. The method of claim 10, wherein intraprostatic injection comprises intralesional injection, transurethral injection, transrectal injection, or transperineal injection.

12. The method of claim 10, comprising administering a single injection of about 1 to 50 ml.

13. The method of claim 10, comprising administering a single injection of about 1 to 5 ml.

14. The method of claim 1, wherein local administration comprises administering a depot formulation.

15. The method of claim 1, wherein local administration comprises administering a slow release implant, a microencapsulated composition, a conjugate with a biodegradable polymer, or a conjugate with a prostate-specific immunoglobulin.

16. A method of degrading a prostate tumor in a mammal comprising local administration to the prostate of a sterile pyrogen-free solution comprising effective concentrations of calcium ions, collagenase, hyaluronidase, a nonionic surfactant, an antibiotic, and a pharmaceutically acceptable aqueous carrier having a physiologic pH; wherein the solution is suitable for administration to living mammals at single or multiple dosages of about 1 to 50 ml via intraprostatic injection; and wherein administration of said solution causes the necrosis, liquification, and regression of said tumor.

17. The method of claim 16, wherein collagenase is provided at a concentration of about 2,500 to 25,000 U/ml.

18. The method of claim 16, wherein hyaluronidase is provided at a concentration of about 1,600 to 16,000 U/ml.

19. The method of claim 16, wherein the nonionic surfactant comprises octylphenoxypolyethoxyethanol.

20. The method of claim 16, wherein the antibiotic comprises gentamicin.

21. The method of claim 16, wherein the intraprostatic injection comprises intralesional injection, transurethral injection, transrectal injection, or transperineal injection.

22. The method of claim 16, comprising administering a single injection of about 1 to 20 ml.

* * * * *

UNITED STATES PATENT AND TRADEMARK OFFICE
CERTIFICATE OF CORRECTION

PATENT NO. : 6,913,744 B2
DATED : July 5, 2005
INVENTOR(S) : Gokcen

It is certified that error appears in the above-identified patent and that said Letters Patent is hereby corrected as shown below:

Column 8,
Line 46, "dose of gentarnicin," should read -- dose of gentamicin, --.
Line 52, "Trimethoprirn/sulfamethoxazole" should read -- Trimethoprim/sulfamethoxazole --.

Column 14,
Line 64, "specific iumunoglobulin." should read -- specific immunoglobulin. --.

Signed and Sealed this

Eighth Day of November, 2005

JON W. DUDAS
*Director of the United States Patent and Trademark Office*